United States Patent
McKee et al.

(10) Patent No.: US 9,594,054 B2
(45) Date of Patent: Mar. 14, 2017

(54) TARGETED DELIVERY OF REAGENTS TO SPOTS ON A PLANAR SUPPORT THROUGH PATTERNED TRANSFER SHEETS

(71) Applicant: Bio-Rad Laboratories, Inc., Hercules, CA (US)

(72) Inventors: Clayton T. McKee, Davis, CA (US); William Strong, El Cerrito, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 563 days.

(21) Appl. No.: 13/950,590

(22) Filed: Jul. 25, 2013

(65) Prior Publication Data

US 2014/0027284 A1 Jan. 30, 2014

Related U.S. Application Data

(60) Provisional application No. 61/675,451, filed on Jul. 25, 2012.

(51) Int. Cl.
*G01N 27/447* (2006.01)

(52) U.S. Cl.
CPC . *G01N 27/44747* (2013.01); *G01N 27/44739* (2013.01)

(58) Field of Classification Search
None
See application file for complete search history.

(56) References Cited

U.S. PATENT DOCUMENTS

| | | | | |
|---|---|---|---|---|
| 4,840,912 A | * | 6/1989 | Glattstein | G01N 33/946 436/901 |
| 5,391,478 A | * | 2/1995 | Greene | G01N 33/54366 422/408 |
| 5,976,813 A | * | 11/1999 | Beutel | G01N 33/54313 422/503 |
| 2004/0091941 A1 | | 5/2004 | Ewing et al. | |
| 2010/0044229 A1 | | 2/2010 | Margalit et al. | |
| 2011/0143365 A1 | | 6/2011 | Buchanan | |
| 2012/0009662 A1 | | 1/2012 | Shen et al. | |
| 2012/0309024 A1 | | 12/2012 | Margalit et al. | |
| 2013/0075261 A1 | | 3/2013 | Margalit et al. | |

FOREIGN PATENT DOCUMENTS

| | | | | |
|---|---|---|---|---|
| CN | 102150045 | | 8/2011 | |
| EP | 2310857 | | 4/2011 | |
| WO | 2005-000811 | | 1/2005 | |
| WO | 2010-006318 | | 1/2010 | |
| WO | 2010-102294 | | 9/2010 | |
| WO | 2011-097412 A1 | | 8/2011 | |
| WO | WO 2011/097413 | * | 8/2011 | ............... B01L 3/00 |
| WO | 2011-144758 A1 | | 11/2011 | |
| WO | WO 2011/144758 A1 | * | 11/2011 | ............... B01L 3/00 |

OTHER PUBLICATIONS

European search and opinion in PCT/US2013/051980 mailed Jun. 3, 2016.*
International Search Report and Written Opinion mailed Dec. 6, 2013 for International Patent Application No. PCT/US2013/5198, 10 pages.
European Search Report mailed Jun. 3, 2016.

* cited by examiner

*Primary Examiner* — Matthew Martin
*Assistant Examiner* — Steven Rosenwald
(74) *Attorney, Agent, or Firm* — Kilpatrick Townsend & Stockton LLP

(57) ABSTRACT

Molecular species that are immobilized in discrete locations on a planar support such as protein bands on a gel or a blotting membrane or species applied in dots or spots on a membrane are reacted with binding reagents that are applied through a porous hydrophilic transfer sheet placed over the planar support, the sheet having at least one region that is laterally bordered by a barrier with the binding reagent retained within the bordered region. The bordered region is placed directly over an area on the planar support where the molecular species are expected to reside if they are present on the support. The binding reagent is then delivered into the support to contact the species. Targeted delivery of the binding reagent is thus achieved with improved efficiency.

5 Claims, No Drawings

TARGETED DELIVERY OF REAGENTS TO SPOTS ON A PLANAR SUPPORT THROUGH PATTERNED TRANSFER SHEETS

CROSS-REFERENCES TO RELATED APPLICATIONS

This application claims the benefit under 35 U.S.C. §1.119(e) of U.S. provisional Application No. 61/675,451, filed Jul. 25, 2012, the contents of which are incorporated by reference in the entirety.

BACKGROUND AND SUMMARY OF THE INVENTION

1. Field of the Invention

This invention resides in the field of biological binding assays, and relates in particular to the transfer of binding members or other reagents to spots, bands, or other spatial arrays on a membrane, gel, or other planar support for purposes of detection, identification, and quantification.

2. Description of the Prior Art

Proteins, nucleic acids, or other biological species that have been electrophoretically separated in a slab gel are often transferred to a membrane of nitrocellulose, nylon, polyvinyl difluoride, or similar materials for identification and quantification since these steps are more easily performed on the membrane than in the gel. A common transfer technique is electroblotting, in which the flat surfaces of the gel and membrane are placed in direct contact and an electric current is passed through both the gel and the membrane in a transverse direction, thereby transferring the species in a manner similar to that by which the species were mobilized within the gel. When the species are DNA fragments, the transfer is termed a Southern blot after its originator, the British biologist Edwin M. Southern. By analogy, the transfer of RNA fragments is termed Northern blotting, and the transfer of proteins or polypeptides is termed Western blotting. Still further examples are "Eastern" blots for post-translational modifications, and "Far Western" blots for protein interactions.

Electroblotting of all of these types can be performed in either a wet, dry, or semi-dry format. In wet blotting, the gel and membrane are layered over each other in a stack which is immersed in a transfer buffer solution in a tank on whose walls are mounted wire or plate electrodes. The electrodes are then energized to cause the solutes to migrate from the gel to the membrane. In semi-dry blotting, filter papers wetted with the transfer buffer solution are used, and the stack contains the filter papers on the top and bottom with the gel and the membrane between the filter papers to form a "blotting sandwich." The electrodes are then placed in direct contact with the exposed surfaces of the wetted filter papers. Dry electroblotting uses no liquid buffers other than those residing in the gels. Descriptions of wet, dry, and semi-dry electroblotting and the associated materials and equipment are found in Margalit et al. (Invitrogen) United States Patent Application Publication Nos. US 2006/0272946 A1, published Dec. 7, 2006, US 2006/0278531 A1, published Dec. 14, 2006, and US 2009/0026079 A1, published Jan. 29, 2009; Littlehales (American Bionetics) U.S. Pat. No. 4,840,714, issued Jun. 20, 1989; Dyson et al. (Amersham International) U.S. Pat. No. 4,889,606, issued Dec. 26, 1989; Schuette (Life Technologies, Inc.), U.S. Pat. No. 5,013,420, issued May 7, 1991; Chan et al. (Abbott Laboratories), U.S. Pat. No. 5,356,772, issued Oct. 18, 1994; Camacho (Hoefer Scientific Instruments), U.S. Pat. No. 5,445,723, issued Aug. 29, 2005; Boquet (Bertin & Cie), U.S. Pat. No. 5,482,613, issued Jan. 9, 1996; and Chen (Wealtec Enterprise Co., Ltd.) U.S. Pat. No. 6,592,734, issued Jul. 15, 2003.

Regardless of whether electroblotting is performed in a wet, dry, or semi-dry format, the resulting electroblot is further treated with detection reagents to render the biological species in the blot detectable by methods appropriate to the species themselves. In Southern and Northern blots, for example, the detection reagents are hybridization probes monitored by detection of a fluorescent or chromogenic dye. In Western blots, the detection reagents can include primary antibodies followed by the use of a secondary antibody labeled with a fluorophore, a chromophore, or an enzyme to detect the antibodies. Alternatively, the secondary antibody can be labeled with a detection agent such as biotin or avidin/streptavidin, and the presence or absence of the detection agent can be detected. Similar or analogous procedures, known among skilled biochemists, are performed with Far Western blots and Eastern blots.

Spatial arrays other than electroblots are also used in biological assays. Binding assays can be performed directly on slab gels, for example, as well as mass spectroscopy targets, ELISA plates, and on proteins, nucleic acids, or other biological species that have been deposited on a membrane or other support surface in regularly spaced or irregularly spaced two-dimensional arrays by electrospraying, vacuum deposition, pin spotting, and other methods.

In all of these spatial arrays, the binding reagents that are applied to the spots, including detection reagents, hybridization probes, antibodies, or other species, are a significant component of the cost of these procedures, and much of the volume of any given reagent is wasted since the bands or spots where binding is to occur occupy but a small fraction of the surface area of the support. One way to limit the cost is to use a highly diluted form of the binding reagent, but this requires a prolonged contact time which places a limit on the number of analyses that can be performed in a given period.

SUMMARY

It has now been discovered that a binding reagent can be applied to spotted species on a planar surface in a highly efficient manner by using a porous hydrophilic transfer sheet that contains the binding reagent in a region of the sheet that is laterally delimited. The sheet can be laterally delimited by a barrier. Suitable barriers include hydrophobic barriers such as wax barriers, or barriers created by vapor or liquid phase silanization of the porous hydrophilic transfer sheet. Suitable barriers also include impermeable barriers. Such impermeable barriers include barriers comprising a plastic, polymer, or resin. In some cases, the impermeable barriers are frames that support a hydrophilic transfer sheet suspended within the frame.

In some cases, the barriers are comprised of a combination of hydrophobic (e.g., wax or silanized cellulose) and impermeable barriers. For example, in some cases, the porous hydrophilic transfer sheets are surrounded by impermeable (e.g., plastic or resin) barrier frames and are further subdivided by wax or silanized cellulose barriers.

Application to the spotted species can then be achieved by placing the transfer sheet in contact with the planar surface under conditions causing transfer of the binding reagent onto the surface. The binding member can fill the delimited region by diffusion without crossing the barrier, and upon contact of the transfer sheet with the spotted surface, the binding member will limit its contact to the spots, or to small areas that include the spots, that are aligned with the region. Transfer from the sheet to the spots can occur by simple diffusion or it can be induced by any of various known methods such as electroblotting. To direct the reagent to an analyte of interest at a desired location on a blotting membrane, for example, the porous sheet is positioned such that the delimited region is aligned with the location on the membrane that the analyte will occupy if present. Alignment can be achieved by various known means such as aligning marks or features on the membrane and porous sheet.

In some embodiments, the reagent can be delivered in a directed fashion such that the transfer sheet contains a binding reagent in a laterally delimited region and transfers the binding reagent to a laterally delimited region of a planar surface that is not horizontally aligned with the laterally delimited region of the transfer sheet. For example, the barrier defining the laterally delimited region can form one or more channels that direct the flow of the binding reagent during transfer. As another example, transfer can be effected from the transfer sheet, through one or more additional hydrophilic sheets with offset laterally delimited hydrophilic regions to the planar surface. As yet another alternative, a first and a second transfer sheet, each with laterally delimited regions that only partially penetrate each of the transfer sheets can be placed against each other to create a horizontal channel. The horizontal channel can then direct transfer of a binding reagent from the first transfer sheet to a region on the planar support that does not align with the first transfer sheet.

The delimited region can be of millimeter-sized proportions (e.g., 10 mm or less), micron-sized (e.g., 100 microns or less) even submicron-sized), and can be substantially the width of a single lane in an electroblot, a single band spanning in a series of parallel lanes, a portion of a lane (in which two or more regions with different detection reagents can be placed over different segments of a single lane), or any small region that limits its area of contact to a specific area of interest on the blotting membrane. The same will be true for application to gels or any other surface containing bands or spots of molecular species of potential interest. In some cases, the delimited region is substantially the width of 1, 2, 3, 4, 5, 6, 7, 8, 9, 10, 11, 12, 13, 14, 15 or more lanes in an electroblot.

The transfer sheet can contain an array of circular, rectangular, square, etc. delimited regions of any size. For example, the transfer sheet can be an array of circular delimited regions. In some cases, the array of circular delimited regions is of suitable dimensions for transfer of one or more binding reagents to one or more wells of a microtiter or ELISA plate (e.g., a 6, 12, 24, 48, 96, 384, or 1536 well microtiter or ELISA plate). Similarly, each of the delimited regions can be further subdivided into smaller regions for multiplex delivery of reagent to each spot, well, or location in an array.

With this method, it is no longer necessary to coat the entire spotted surface with the binding reagent, and the method thereby allows the binding reaction to occur with a much smaller quantity of binding reagent. The method also allows different regions of the spotted surface to be treated with different binding reagents or with the same binding reagent at different concentrations or dilutions. The use of two or more binding reagents in different regions of the porous sheet enables the user to detect different spotted species simultaneously, for example, when the species are detected by different reactions, while the use of the same binding reagent at different concentrations or dilutions allows the user to determine by simultaneous tests the most appropriate dilution for a given analyte in a given sample. Other uses and advantages will be readily apparent to those of skill in the art.

A hydrophobic wax barrier can be formed by manually drawing, printing, or otherwise forming an outline of the desired region in wax to the surface of the porous sheet, then heating the sheet to liquefy the wax, causing it to penetrate the thickness of the sheet. Outlines of any shape, size, or number can thus be formed and a variety of binding reactions, including individual reactions and comparisons among different reactions, can be performed in a single step.

A hydrophobic barrier can also be formed by vapor or liquid phase silanization. For example, the transfer sheet can be placed in a mask that exposes regions of the transfer sheet to a silanization reagent such as trimethylchlorosilane. The silanization reagent can then be contacted with the sheet and the laterally delimited region or regions formed. The laterally delimited region can then be contacted with an aqueous solution containing a binding reagent, thereby making transfer sheet with an aqueous-based binding reagent that is reversibly immobilized in a laterally delimited region that is bordered by a barrier.

In some embodiments, the invention provides a kit comprising a container and 1, 2, 3, 4, or more porous hydrophilic sheets residing therein, the porous hydrophilic sheets each having 1, 2, 3, 4, or more laterally delimited regions therein that are bordered by a hydrophobic or impermeable barrier. In some cases, the porous hydrophilic sheets each have 1, 2, 3, 4, or more binding reagents reversibly immobilized therein. The binding reagents can be antibodies. The laterally delimited regions can be substantially the width of 1, 2, 3, 4, 5, 6, 7, 8, 9, 10, 11, 12, 13, 14, 15 or more lanes in an electroblot. The container can be configured to protect the porous hydrophilic sheets from light and/or moisture.

In some cases, the kit further comprises a transfer buffer, such as a Western blot transfer buffer. In some cases, the kit can comprise a component of a transfer buffer. In some cases, the kit further comprises a transfer enhancing reagent such as a surfactant, cyclodextrin, polyol, simple sugar, polysaccharide, organic solvent, aggregation modifying protein, disordered peptide sequence, amino acid, oxido-reductant, lyoprotectant, cryoprotectant, or chaotropic agent.

Other objects, embodiments, features, and advantages will be apparent from the description that follows.

DETAILED DESCRIPTION OF SELECTED EMBODIMENTS

For aqueous-based binding reagents, such as antibodies, nucleic acid probes, and many other types of reagents, the porous sheet will be a sheet of hydrophilic sorbent material such as common laboratory blotting paper or filter paper, or any hydrophilic form of cellulose, polyester, or cellulose-polyester blends. An example of a cellulose paper is Whatman Chromatography Paper (GE Healthcare, Piscataway, N.J., USA). Examples of polyesters suitable for the sheet are those sold under the trademarks VWR SPEC-WIPE® (VWR International, Leicestershire, United Kingdom); ANTICON® and ANTICON® MILLISEAL® (Milliken & Company, LaGrange, Ga., USA); VECTRA® ALPHA®, ALPHAWIPE®, ALPHASORB®, ALPHA10®, and MIRACLE WIPE® (ITW-Texwipe Company, Mahwah, N.J., USA); and ULTRASEAL® and VALUSEAL™ (Berkshire Corporation, Great Barrington, Mass., USA). Examples of polyester-cellulose blends suitable for use are those sold under the trademarks DURX® and MICROFIRST® (Berkshire Corporation, Great Barrington, Mass., USA); C1 Wiper and PROZORB® (Contec, Spartanburg, S.C., USA); and TECHNI-CLOTH® (ITW-Texwipe Company, Mahwah, N.J., USA).

The wax used to form the wax barriers can be any wax that is flowable at elevated temperatures and non-flowable at ambient temperature (20-25° C.). Examples are paraffin waxes, microcrystalline waxes, thermoset waxes, animal waxes such as beeswax, lanolin, and tallow, vegetable waxes such as soy, carnauba, candelilla and palm waxes, mineral waxes such as ceresin and montan waxes, petroleum waxes, and synthetic waxes such as ethylenic polymers, chlorinated naphthalenes, and Fischer-Tropsch waxes. Paraffin wax compositions may contain, in addition to n-paraffins and isoparaffins, minor amounts of cyclo-paraffins or olefins, or both. Waxes that become flowable, i.e., that have melting points, within the temperature range of from about 60° C. to about 150° C., or in certain cases, from about 75° C. to about 125° C., are among those that can be used. Wax formulations and compositions that behave in this manner are known to those of skill in the art.

The silanization reagent used to form hydrophobic barriers can be any silanization reagent that reacts with the hydrophilic transfer sheet. For example, if the hydrophilic transfer sheet contains cellulose, a silanization reagent that silanizes hydroxyl groups of the cellulose backbone can be utilized. Exemplary silanization reagents include, but are not limited to, trimethylchlorosilane, trimethylsilane, hexamethyldisilazane, Silanization reagents further include triethoxysilanes ($R-Si(C_2H_5O)_3$) where R is, for example, vinyl, methacrylol, aminopropyl, fluoroalkyl, or thioethyl. Other suitable silanization reagents will be readily apparent to those of skill in the art.

The wax or other delimiting reagent (e.g., silanization reagent, or impermeable barrier) can be applied to one side or both sides of the porous sheet, although in most cases, application to one side will be sufficient. The delimiting reagent can be applied as a liquid. The liquid can be applied by hand or other apparatus. In some cases, the liquid is sprayed or poured onto the transfer sheet. Spraying can be accomplished with an inkjet printer or similar apparatus. In some cases, the liquid hardens after application to form an impermeable and/or hydrophobic barrier. Alternatively, the delimiting reagent can be applied as a vapor. For example, a silanization reagent, wax, plastic, resin, or polymer can be applied as a vapor that condenses on the transfer sheet or reacts with the transfer sheet. Alternatively, the delimiting reagent can be applied as a solid. For example, wax can be applied as a solid as described herein. In some cases, the transfer sheet is masked to protect regions from delimiting reagent, and the delimiting reagent is contacted with the transfer sheet.

Application of wax can be achieved by hand, either by the use of a common crayon or by a wax pen, or by a wax printer. Wax pens are known in the art and commonly include a housing having a reservoir to contain hot wax, a spout, and a handle. Application of the hot wax is achieved by tipping the housing to cause the liquefied wax to pass through the spout, and the housing is equipped with a valve to stop the flow of the wax at the terminus of a printed line. Wax printers are likewise known in the art and commonly operated by thermal transfer printing using a print head that includes an array of very small heating elements that are software-controlled for independent activation to produce localized heating of the wax above its melting point to release the wax to the print medium. Commercially available examples of wax printers include the Phaser 8560DN (Fuji Xerox, Ltd., Japan), and the CALCOMP COLORMASTER PLUS thermal wax transfer printer (CalComp Graphics, LLC, Foothill Ranch, Calif., USA). Descriptions of wax printers and their use can be found in Kroon (Tektronix, Inc.), U.S. Pat. No. 5,957,593 (Sep. 28, 1999); Lin (Xerox Corporation), U.S. Pat. No. 8,206,664 (Jun. 26, 2012); Lu, Y., et al., "Rapid prototyping of paper-based microfluidics with wax for low-cost, portable bioassay," *Electrophoresis* 2009, 30, 1497-1500; and Carrilho, E., et al., "Understanding Wax Printing: A Simple Micropatterning Process for Paper-Based Microfluidics," *Anal. Chem.,* 2009, 81 (16), 7091-7095. The width of a wax line as applied (prior to heating) can vary and is not critical to the present invention, provided that the amount of wax contained within the line is sufficient to penetrate the porous sheet and form a barrier to the lateral flow of aqueous fluid within the sheet.

Once applied, the wax can be made to penetrate the bulk thickness of the porous sheet to fill the pores and form a lateral barrier to aqueous fluid flow by heating the wax above its melting point. The amount of wax applied will be such full penetration of the thickness of the sheet with the melted wax will occur while lateral flow of the melted wax (i.e., in directions parallel to the flat faces of the sheet) is minimal or at least limited to a small distance that is substantially uniform along the length of a line of applied wax so that the resulting area bordered by the wax barrier is known and controlled. The formation of the barrier in this manner can also be controlled by the degree of heating, including the temperature to which the wax is heated and the length of time that the heating is continued. Optimal temperatures and durations are readily determinable by routine trial and error, but in most cases serviceable results will be obtained by heating to at least 5 degrees Celsius above the wax melting point, and in many cases from about 5 to about 50 degrees Celsius above the melting point, or from about 10 to about 30 degrees Celsius above the melting point. The most appropriate heating time will depend on the temperature, higher temperatures requiring less time. In general, heating times ranging from about fifteen seconds to about twenty minutes, or in many cases from about thirty seconds to about ten minutes, will provide useful results. Heating can be achieved by conventional means, including radiative heating, conductive heating, convective heating, and microwave heating. Effective results can be achieved with equipment as simple as a hot plate or a conventional oven.

Optimal widths for hydrophobic or impermeable barriers may vary with the dimensions of the area to be bordered by the barrier and with the thickness of the sheet and are readily determinable by routine testing. In most cases, the width will range from about thirty microns to about 3 mm, from about 100 microns to about 1 mm, or from about 200 microns to about 5 mm, or 10 mm.

The barrier can be formed along the periphery of the sheet, in which case the region of the sheet delimited by the barrier is the entire length and width of the sheet (or diameter in case of a circular sheet) except for a narrow strip around the edge. Sheets of this type can be formed for example as a series of individual narrow strips placed side-by-side on the surface of the blotting membrane. Strips that are pre-loaded with different detection reagents or detection reagents at different dilutions can be prepared by a reagent supplier and selected and combined by the user to meet the particular needs of an experiment or an analysis. Alternatively, multiple regions can be formed in a single sheet, either as parallel lanes or as an array of spots, each isolated from the others by the hydrophobic barriers. The regions can be pre-loaded by the supplier as standard arrays or loaded at the point of use by the user to tailor the regions to meet the user's individual needs.

The patterned and reagent-bearing porous sheets described herein can be obtained and used, therefore, in various ways. These include purchasing porous sheets that have pre-formed barriers and that are pre-loaded with detection reagents from a supplier, as well as purchasing porous sheets that have pre-formed barriers and then impregnating the bordered regions with detection reagents at the point of use, and still further, purchasing porous sheets with neither barriers nor detection reagents, allowing the user to both form the barriers and add the reagents at the point of use. In some embodiments, a pre-loaded sheet can be selected by a user and contacted with an eluent to provide a single dose of binding reagent.

Porous sheets can be provided or purchased as kits containing one sheet or multiple sheets (e.g., at least about 2, 3, 4, 5, 6, 7, 8, 9, 10, 11, 12, 13, 14, 15, 20, 25, 30, 40, 50, 60, 75, 100 or more). The kits can also contain one or more binding reagents (e.g., in a separate container or impregnated into one or more sheets). In some embodiments, the sheets with binding reagent stored therein can be stored at room temperature (e.g., at least about 8, 10, 12, 14, 16, 18, 20, 22, 24, 25, 27, 28, or 30° C.) for at least about 1, 2, 3, 4, 5, 6, 7 days or 1, 2, 3, 4, 5, 6, 7 weeks, or 1, 2, 3, 4, 5, 6, 7, 8, 9, 10, 11, 12 months or longer. The sheets can each contain one or more laterally delimited regions as described herein.

The kits can contain one or more sheets that are substantially the width of 1, 2, 3, 4, 5, 6, 7, 8, 9, 10, 11, 12, 13, 14, 15, or more lanes of an electroblot. Alternatively, or in addition, the kit can contain one or more sheets that have laterally delimited regions that are substantially the width of 1, 2, 3, 4, 5, 6, 7, 8, 9, 10, 11, 12, 13, 14, 15, or more lanes of an electroblot. In some cases, the kits can contain one or more sheets that are substantially the shape and/or size of one or more spots, wells, or locations of an array. In other cases, the kits can contain one or more sheets that have laterally delimited regions that are substantially the shape and/or size of one or more spots, wells, or locations of an array. For example, the kit can contain one or more sheets that have 6, 12, 24, 48, 96, 384, or 1536 laterally delimited regions for delivery of one or more binding reagents to one or more of the 6, 12, 24, 48, 96, 384, or 1536 wells of a microtiter plate.

Moreover, a user can submit a design to a supplier for custom manufacture of a sheet. The custom sheet can contain a specified barrier pattern. Alternatively, or in addition, the custom sheet can contain user-specified binding reagents. The binding reagents can have specificity for or bind to user-specified targets such as target proteins or control proteins (e.g., actin, tubulin, GAPDH, etc.).

The kits can include a container in which one or more porous hydrophilic sheets are delivered from a manufacturer or supplier or stored by a user. In some cases, the container is configured to protect the porous hydrophilic sheets from moisture and/or light. In some cases, the container is configured to protect the porous hydrophilic sheets from drying out. Exemplary containers include foil pouches or plastic trays with a sealed cover that is removable by the end-user.

In some embodiments, the kits can include a transfer buffer, a transfer buffer concentrate (e.g., 2x, 3x, 4x, 5x, 10x, 100x transfer buffer), or one or more components of a transfer buffer. In some cases, the kit can include one or more transfer enhancing agents. In some cases, the one or more transfer enhancing agents can be provided as a component of a transfer buffer. Suitable transfer enhancing agents include, but are not limited to detergents or surfactants (anionic, cationic, ionic, zwitterionic, or non-ionic), cyclodextrins, simple sugars, polysaccharides, polyols, organic solvents, aggregation modifying proteins, disordered peptide sequences, amino acids, oxido-reductants, lyoprotectants, cryoprotectants, and chaotropic agents as described herein.

The kits can be used by any of the methods described herein. For example, a kit can be obtained (e.g., purchased or manufactured) and a porous hydrophilic sheet obtained therefrom. In some cases, a porous hydrophilic sheet from the kit can then be impregnated with one or more binding reagents. In some cases, one or more laterally delimited regions can then be imprinted onto a porous hydrophilic sheet from the kit. Alternately, a porous hydrophilic sheet from the kit that already contains one or more binding reagents or laterally delimited regions can be obtained. In some cases, the porous hydrophilic sheet can then be used to transfer one or more binding reagents to a planar support, such as a western blot membrane.

Transfer from the sheet to the membrane can occur by simple diffusion, by capillary action, by vacuum blotting, or by electrotransfer. Simple diffusion can be achieved by simple contact of the reagent-bearing porous sheet with the blotting membrane without intervening sheets. Depending on the materials and their quantities and the thicknesses of the sheets, diffusive transfer can be achieved for example within a time period of from about five minutes to about 3 hours, or in many cases from about thirty minutes to about two hours. Capillary blotting is achieved by placing a stack of wet paper (i.e., paper wetted with water or an aqueous buffer solution) above the reagent-bearing sheet and a stack of dry paper below the membrane, or any porous hydrophilic material in place of the stacks of paper. Capillary action draws the water from the upper stack through the reagent-bearing sheet and the membrane into the lower stack, dissolving the reagent as it passes through the reagent-bearing sheet and depositing the reagent in the membrane as the reagent couples with the analytes in the membrane. The wet and dry sheets may be replaced one or more times to increase the efficiency. Vacuum blotting is performed by placing a stack of wet paper above the reagent-bearing sheet as in capillary blotting and applying a vacuum (or partial vacuum) beneath the membrane. The water or aqueous buffer thus travels through the sheets by pressure differential, dissolving and depositing the reagent as in capillary blotting but at a faster rate. Electroblotting is performed by placing electrodes above the reagent-bearing sheet and below the membrane, with intervening wetted sheets as desired. The electrodes are energized to impose a voltage difference across the contacting sheets in the direction parallel to the direction of transfer and with a polarity appropriate to causing electrophoretic migration of the detection reagent across the interface between the sheet and the membrane. Binding reagents that bear an electric charge will migrate under such a voltage difference, and the procedure can be analogous to the blotting procedure by which the species on the blotting membrane were transferred to the membrane from the medium in which they were initially separated from each other, for example, a slab gel in which one-dimensional or two-dimensional electrophoresis was performed, and further analogous to the native polyacrylamide gel electrophoresis. Thus, sheets of absorbent material wetted with buffer solutions can be placed on the two outer sides of the porous sheet-blotting membrane stack and electrodes in contact with the buffer-wetted outer sheets can be energized to pass an electric current through the stack.

The transfer of binding reagents, such as primary and secondary antibodies, can be further enhanced by including zwitterionic surfactants that do not denature the antibodies. For example, the zwitterionic surfactants can be included in a transfer buffer solution or dried onto the porous hydrophilic sheet. Further compositions useful for enhancing transfer of binding reagents from a porous hydrophilic transfer sheet include cyclodextrins, non-ionic surfactants, ionic surfactants, simple sugars, polysaccharides, polyols, organic solvents, aggregation modifying proteins, disordered peptide sequences, amino acids, oxido-reductants, lyoprotectants, cryoprotectants, and chaotropic agents.

Cyclodextrins include, but are not limited to, α-cyclodextrin, β-cyclodextrin, γ-cyclodextrin, (2,3,6-tri-O-methyl)-β-cyclodextrin, (2,3,6-tri-O-methyl)-β-cyclodextrin, (2-hydroxy)propyl-β-cyclodextrin, (2-hydroxy)propyl-γ-cyclodextrin, random methyl-β-cyclodextrin, random methyl-γ-cyclodextrin, carboxymethyl-β-cyclodextrin, carboxymethyl-γ-cyclodextrin, 6-monodeoxy-6-monoamino-β-cyclodextrin, sulfobutyl-β-cyclodextrin, 6-amino-6-deoxy-β-cyclodextrin, acetyl β-cyclodextrin, succinyl α-cyclodextrin, succinyl β-cyclodextrin, succinyl γ-cyclodextrin, (2,3,6-tri-O-benzoyl)-β-cyclodextrin, succinyl-(2-hydroxypropyl)-β-cyclodextrin, and succinyl-(2-hydroxypropyl)-γ-cyclodextrin. Cyclodextrins can also include cyclodextrin polymers containing one or more of the foregoing cyclodextrin molecules. Additional cyclodextrins are known in the art, and include, e.g. those described on the world wide web at cyclodextrin.com. Exemplary concentrations of cyclodextrins include, but are not limited to about 1 mM, 2 mM, 2.5 mM, 5 mM, 7.5 mM, 10 mM, 15 mM, 20 mM, 25 mM, 50 mM, 75 mM, or 100 mM.

Non-ionic surfactants include polyethylen-sorbitan-fatty acid esters, polyethylene-polypropylene glycols and polyoxyethylene-stearates. Polyethylen-sorbitan-fatty acid esters include polyethylen(20)-sorbitan-esters (Tween 20™) and polyoxyethylene(20)-sorbitanmonooleate (Tween 80™). Polyethylene-polypropylene glycols include polyoxypropylene-polyoxyethylene block co-polymers such as those sold under the names Pluronic® or Poloxamer™. Polyoxyethylene-stearates include those sold under the trademark Myrj™. Polyoxyethylene monolauryl ethers include those sold under the trademark Brij™, e.g., Brij-35. Exemplary concentrations of non-ionic surfactants include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Ionic surfactants include anionic surfactants and cationic surfactants. Anionic surfactants useful in the present invention include, but are not limited to soaps including alkali soaps, such as sodium, potassium and ammonium salts of aliphatic carboxylic acids, usually fatty acids, such as sodium stearate. Additional anionic surfactants include organic amine soaps such as organic amine salts of aliphatic carboxylic acids, usually fatty acids, such as triethanolamine stearate. Cationic surfactants useful in the present invention include, but are not limited to, amine salts such as octadecyl ammonium chloride and quarternary ammonium compounds such as benzalkonium chloride. Ionic surfactants further include the sodium, potassium and ammonium salts of alkyl sulfates, such as sodium dodecyl sulfate and sodium octyl sulfate. Exemplary concentrations of ionic surfactants include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Zwitterionic surfactants have both cationic and anionic centers attached to the same molecule. The cationic part is, e.g., based on primary, secondary, or tertiary amines or quaternary ammonium cations. The anionic part can include sulfonates, as in CHAPS (3-[(3-Cholamidopropyl)dimethylammonio]-1-propanesulfonate). Other anionic groups are sultaines illustrated by cocamidopropyl hydroxysultaine and betaines, e.g., cocamidoethyl betaine, cocamidopropyl betaine, or lauramidopropyl betaine. Exemplary concentrations of zwitterionic surfactants include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Non detergent sulfobetaines (NDSBs) have a sulfobetaine hydrophilic group and a short hydrophobic group that cannot aggregate to form micelles, therefore NDSBs are not considered detergents. NDSBs include, but are not limited to NDSB 256, NDSB 221, NDSB 211, NDSB 201, NDSB 195, 3-(4-tert-Butyl-1-pyridinio)-1-propanesulfonate, 3-(1-pyridinio)-1-propanesulfonate, 3-(Benzyldimethylammonio) propanesulfonate, and Dimethylethylammoniumpropane sulfonate. Exemplary concentrations of NDSBs include, but are not limited to about 0.01%, 0.02%, 0.05%, 0.1%, 0.2%, 0.5%, 0.75%, 1%, 2%, 2.5%, 5%, 7.5%, and about 10% w/w, w/v, or v/v.

Polyols are compounds with multiple hydroxyl functional groups. In some cases, polyols can modify the aggregation or denaturation behavior of a protein by a variety of mechanisms. For example, in some cases, the polyol can shift the equilibrium to the folded state by presenting a thermodynamically disfavored interaction with the protein backbone. Alternatively, in some cases, the polyol can bind to and stabilize the folded state of the protein.

Polyols can include simple sugars such as sucrose, mannitol, sorbitol, inositol, xylitol, erythritol, glucose, galactose, raffinose, and trehalose. Polyols can also include polysaccharides such as dextran, starch, hydroxyethyl starch, and polymers containing the simple sugars described herein. Polyols can also include glycerol, ethylene glycol, polyethylene glycol, pentaerythritol propoxylate, and pentaerythritol propoxylate, and combinations thereof.

Organic solvents include, but are not limited to, those organic solvent that are known to inhibit denaturation, unfolding, or aggregation of one or more proteins. A variety of suitable organic solvents are known in the art. For example, organic solvents can include ethanol, butanol, propanol, phenol, dimethyl formamide, 2-methyl-2,4-pentanediol, 2,3-butanediol, 1,2-propanediol, 1,6-hexanediol, and dimethyl sulfoxide.

Aggregation modifying proteins include proteins known in the art to inhibit denaturation, unfolding, or aggregation of one or more proteins. Aggregation modifying proteins include, but are not limited to, albumins. Albumins are proteins that are water-soluble, are moderately soluble in concentrated salt solutions, and experience heat denaturation. Albumins include serum albumins (e.g., bovine, horse, or human serum albumin) and egg albumin (e.g., hen egg-white albumin). Aggregation modifying proteins also include casein, gelatin, ubiquitin, lysozyme, and late embryogenesis abundant (LEA) proteins. LEA proteins include LEA I, LEA II, LEA III, LEA IV, LEA V, and atypical LEA proteins. LEA proteins are known in the art and described, e.g., in Goyal K., et al., Biochemical Journal 288 (pt. 1), 151-57, (2005).

Compositions useful for enhancing transfer of binding reagents from a porous hydrophilic transfer sheet include amino acids. In some cases, the amino acids can serve an oxido-reduction function to maintain an appropriate oxidative potential for the protein immobilized on the substrate. Suitable oxido-reducitve amino acids include cysteine and cystine. Other amino acids serve to reduce denaturation or aggregation through a non-oxido-reductive method. For example, arginine, glycine, proline, and taurine have been shown to reduce protein aggregation.

Other oxido-reduction agents can be employed to enhance transfer of binding reagents from a porous hydrophilic transfer sheet. For example, oxido-reductants other than cysteine and cystine, can be used to optimize the reduction potential in the substrate onto which the protein is immobilized. Additional oxido-reductants include mercaptoethanol, dithiothreitol, dithioerythritol, tris(2-carboxyethyl) phosphine, glutathione, glutathione disulfide, and oxidized derivatives thereof, as well as $Cu^{2+}$.

Other compositions useful for enhancing transfer of binding reagents from a porous hydrophilic transfer sheet can also include lyoprotectants, cryoprotectants, or chaotropic agents. In some cases, the chaotropic agent is as urea, thiourea, guanidinium, cyanate, thiocyanate, trimethylammonium, tetramethylammonium, cesium, rubidium, nitrate, acetate, iodide, bromide, trichloroacetate, or perchlorate. Under certain conditions, such as at low concentrations, chaotropes can reduce protein aggregation. Other transfer enhancing compositions include trimethylamine N-oxide.

Compositions useful for enhancing transfer of binding reagents from a porous hydrophilic transfer sheet further include salts. Salts include, but not limited to, the sodium, potassium, magnesium, and calcium salts of chloride, sulfate, and phosphate. Compositions useful for enhancing transfer of binding reagents from a porous hydrophilic transfer sheet also include buffering agents. Exemplary buffering agents include, but are not limited to, tris (hydroxymethyl) amino methene (TRIS), TAPSO, MES, HEPES, PIPES, CAPS, CAPSO, MOPS, MOPSO, and sodium or potassium phosphate, carbonate, bicarbonate, citrate, acetate, or borate buffers.

Compositions useful for enhancing transfer of binding reagents from a porous hydrophilic transfer sheet can be provided in any suitable concentration, such as the concentrations described herein. In some cases, the concentration refers to the concentration of the transfer enhancing composition during the transfer process. In some cases, a binding reagent is provided to the hydrophilic transfer sheet or delivered from the hydrophilic transfer sheet as an aqueous solution containing the binding reagent and one or more transfer enhancing compositions. In some cases, the solution can be contacted with a hydrophilic transfer sheet and, optionally, dried. Alternatively, a hydrophilic transfer sheet containing a binding reagent, and optionally a transfer enhancing composition, can be contacted with a solvent (e.g. water or a buffered aqueous solution), and the binding reagent delivered therefrom. In some cases, the solvent and one or more transfer enhancing compositions are components of a transfer buffer such as a Western blot transfer buffer. Exemplary concentrations of transfer enhancing compositions in the solvent or the aqueous binding reagent solution include, but are not limited to, about 0.001%, 0.005%, 0.01%, 0.05%, 0.1%, 0.5%, 1%, 2%, 4%, 5%, 10%, 20%, or about 25% or more w/v of the solution. Further exemplary concentrations include, but are not limited to, about 1 µM, 5 µM, 10 µM, 25 µM, 50 µM, 75 µM, 100 µM, 150 µM, 200 µM, 300 µM, 500 µM, 750 µM, 1 mM, 5 mM, 10 mM, 25 mM, 50 mM, 100 mM, 150 mM, 200 mM, 300 mM, 500 mM, and 1 M.

In some cases, the compositions useful for enhancing transfer of binding reagents from a porous hydrophilic transfer sheet are provided on the porous hydrophilic transfer sheet. Exemplary compositions containing a composition useful for enhancing transfer of binding reagents from a porous hydrophilic transfer sheet include, porous hydrophilic transfer sheets that contain about 0.001%, 0.005%, 0.01%, 0.05%, 0.1%, 0.5%, 1%, 2%, 3%, 4%, 5%, or about 10%, 20%, or about 25% by weight of one or more transfer enhancing compositions.

Compositions useful for enhancing transfer of binding reagents from a porous hydrophilic transfer sheet can be provided in any suitable combination. For example, in some cases, 1, 2, 3, 4, 5, 6, 7, 8, 9, 10 or more of the foregoing protein transfer enhancing compositions can be utilized to enhance transfer from a hydrophilic transfer sheet. In some cases, prior to contacting the hydrophilic transfer sheet with a solution containing a binding reagent, the substrate contains a transfer enhancing composition, and the solution contains a different transfer enhancing composition. In other cases, the transfer sheet contains a transfer enhancing composition and the binding reagent solution contains the same transfer enhancing composition. In some cases, prior to contacting the hydrophilic transfer sheet with the solution containing the binding reagent, the hydrophilic transfer sheet contains a transfer enhancing composition, and the solution containing the binding reagent does not contain a transfer enhancing composition. In some cases, prior to contacting the transfer sheet with the solution containing the binding reagent, the solution contains a transfer enhancing composition and the substrate does not.

In some embodiments, the hydrophilic transfer sheet contains a gradient of one or more transfer enhancing compositions. In some cases, one or more binding reagents reversibly immobilized on the hydrophilic transfer sheet will thus be transferred with varying efficiency based on its location in the gradient. Thus, a hydrophilic transfer sheet can transfer different concentrations of binding reagent.

As noted above, the binding reagents that are retained within the barriers will be aqueous-based, i.e., suspended or dissolved in aqueous solution, and can include one or more biological agents such as antibodies and enzymes, or detection agents such as avidin, streptavidin, biotin, affinity tags (e.g., 6xHis, or GST), enzyme substrates, fluorescent compounds, colorimetric compounds, chemiluminescent compounds, and radiologic compounds. Conversely, the binding reagents can be antigens and the molecular species on the planar surface can be antibodies. Certain detection protocols entail successive applications of reagents, and in these cases, one or more of the applications can be achieved by use of the porous sheets with delimited reagent regions described herein with the remaining applications made over the entire surface of the planar support, or all applications can be achieved by the successive use of appropriately impregnated sheets. The choice will often depend on which reagents are the most costly. Thus, when detection protocols involve the use of primary and secondary antibodies, primary antibody may be applied to the entire planar support followed by the application of secondary antibody only to the regions bordered by the hydrophobic barriers by using the delimited porous sheets only for the secondary antibody. Conversely, the primary antibody can be applied from the porous sheet by way of the regions bordered by the hydrophobic barriers, and secondary antibody then applied over the entire area of the planar support. Similar procedures with binding reagents other than antibodies will be readily apparent to those of skill in the art. The reagents can also be held in the sheets in dried form (e.g., lyophilized, air dried, etc.) until ready for use. Sheets fully formed with barrier-bordered regions and pre-loaded with lyophilized or otherwise dried reagents can be purchased and stored, and wetted by the user at the point and time of use.

The proteins or other species that are spotted or otherwise immobilized on the planar support will often be components of a biological sample, and the support in these cases will contain one or more spatially separated components of the sample, the spatial separation and particular locations of the component(s) on the support being characteristic of the components themselves and the manner in which their separation or application to the support was achieved. In many cases, the support will be a blotting membrane and the spatial separation will be the result of an electrophoretic procedure performed on the sample. The components of interest in these cases, if present in the sample, will occupy locations on the membrane that are known by virtue of the conditions of the electrophoresis or by comparison with standards of known composition. The components if present will thus often reside in bands at known distances along the length of the gel in which electrophoresis was performed. A single component of the sample can be placed in contact with a binding reagent by the methods described herein, or multiple components of can be placed in contact with the reagent, or a single component over several samples can be placed in contact with the reagent.

In some cases, the porous sheet will be positioned such that the barrier-bordered region containing the binding reagent is aligned with the locations(s) on the blotting membrane where the component of interest will reside if the component was originally present in the sample. "Alignment" in this context means directly above or below when the sheet and membrane are layered horizontally. Alternatively, microchannels formed by the barriers of one or more sheets can direct the flow of the binding reagent from a transfer sheet to an area of the planar support that is not directly above or below the area of the transfer sheet that contains the binding reagent.

When the planar support is a blotting membrane and the species on the planar support are the result of electrotransfer from a gel, the gel and the blotting membrane can be of any irregular or regular shape, such as oval or circular for example, but are typically rectangular. The length and width of a rectangular gel can vary widely, and the thickness will typically be significantly less than, for example 10% or less of, or in many cases 2% or less of, the length or width. Gels of various compositions can be used, including agar gels, starch gels, agarose gels, and acrylamide gels, as well as composite gels of two or more different polymers. The blotting membrane can also be of a variety of materials, examples of which are paper, cellulose derivatives such as cellulose nitrate, cellulose acetate, or nitrocellulose, nylon and nylon-based materials, or polyvinylidene difluoride (PVDF) and PVDF-based materials, and activated or derivatized forms of these materials such as, for example, surface-charged derivatives.

Samples on which the analyses can be performed include biological samples in general, examples of which are plasma, serum, urine, and cerebrospinal fluid. When the array of molecular species is formed by electrophoretic separation and the planar support is either the gel in which the separation was performed or a blotting membrane to which the species separated in the gel have been transferred, separation can have been achieved by any of the many forms of electrophoresis, including one-dimensional slab or capillary electrophoresis, two-dimensional electrophoresis, and isoelectric focusing. All electrophoretic procedures can be performed in conventional ways commonly used in the laboratory and well known in the art, including loading samples onto a gel, the arrangement and use of electrodes and electrode buffers and the energizing of the electrodes at the appropriate polarities.

In systems in which the binding reagent is a dye, any of a wide variety of nucleic acid dyes and protein dyes can be used. Examples are SYPRO dyes, Coomassie dyes, Direct Blue dyes, and copper-based dyes.

In systems using antibodies as detection reagents, many such systems use a sequence of primary antibodies followed by secondary antibodies. Any of the five classes can be used, i.e., IgG, IgA, IgM, IgD, and IgE. Antibody fragments can also be used, such as Fab fragments produced by treating IgG with papain, F(ab')$_2$ produced by treating IgG with pepsin, and a monovalent Fab' fragment produced by treating F(ab')$_2$ with a mild reducing buffer. Monoclonal or polyclonal antibodies can be used. Antibodies can also include single-chain antibodies, diantibodies, or miniantibodies. Antibodies of the invention can also include heavy chain dimers, such as antibodies from camelids or sharks. Since the VH region of a heavy chain dimer IgG in a camelid or shark does not have to make hydrophobic interactions with a light chain, the region in the heavy chain that normally contacts a light chain is changed to hydrophilic amino acid residues. VH domains of heavy-chain dimer IgGs are called VHH (camelid) or VNAR (shark) domains. Antibodies for use in the current invention additionally include single domain antibodies (dAbs) and nanobodies (see, e.g., Cortez-Retamozo, et al., Cancer Res. 64:2853-2857, 2004).

Antibodies that bind to particular proteins or classes of proteins can be used as primary antibodies, and antibodies that bind to other antibodies can be used as secondary antibodies. Thus, antibodies generated from one mammalian species can be used as the primary antibody, and antibodies generated from a second mammalian species that bind to those of the first mammalian species can be used as the secondary antibodies. The species can be rabbit, mouse, goat, sheep, and many others.

Other binding reagents can include affimers, lipocalins (e.g., anticalins), thioredoxin A, bilin binding protein, or a protein containing an ankyrin repeat, the Z domain of staphylococcal protein A, or a fibronectin type III domain.

In systems in which the binding reagent is or includes an enzyme, a wide variety of enzymes and coloimetric or fluorogenic enzyme substrates can be used. Examples of combinations of an enzyme and a colorimetric or fluorogenic substrate are oxidoreductases such as horseradish peroxidase and substrates such as 3,3'-diaminobenzidine (DAB) and 3-amino-9-ethylcarbazole (AEC), which yield a distinguishing color (brown and red, respectively). Other colorimetric oxidoreductase substrates that yield detectable products are 2,2-azino-bis(3-ethylbenzothiazoline-6-sulfonic acid) (ABTS), o-phenylenediamine (OPD), 3,3',5,5'-tetramethylbenzidine (TMB), o-dianisidine, 5-aminosalicylic acid, 4-chloro-1-naphthol. Examples of fluorogenic substrates are homovanillic acid, 4-hydroxy-3-methoxyphenylacetic acid, reduced phenoxazines, reduced benzothiazines, reduced dihydroxanthenes, dihydrofluoresceins, and dihydrorhodamines. Further enzyme-substrate combinations are acid or alkaline phosphatases in combination with 5-bromo-6-chloro-3-indolyl phosphate (BCIP), 6-chloro-3-indolyl phosphate, 5-bromo-6-chloro-3-indolyl phosphate, p-nitrophenyl phosphate, o-nitrophenyl phosphate, 4-methylumbelliferyl phosphate, 6,8-difluoro-7-hydroxy-4-methylcoumarinyl phosphate, fluorescein diphosphate, 3-O-methylfluorescein phosphate, resorufin phosphate, or 9H-(1,3- dichloro-9,9-dimethylacridin-2-one-7-yl) phosphate (DDAO phosphate). Still further enzymes are glycosidases, in particular beta-galactosidase, beta-glucuronidase and beta-glucosidase. Substrates for these enzymes include 5-bromo-4-chloro-3-indolyl beta-D-galactopyranoside (X-gal), o-nitrophenyl beta-D-galactopyranoside (ONPG), p-nitrophenyl beta-D-galactopyranoside, resorufin beta-D-galactopyranoside, fluorescein digalactoside (FDG), fluorescein diglucuronide and their structural variants, 4-methylumbelliferyl beta-D-galactopyranoside, carboxyumbelliferyl beta-D-galactopyranoside and fluorinated coumarin beta-D-galactopyranosides. Still further enzymes are hydrolases such as cholinesterases and peptidases, oxidases such as glucose oxidase and cytochrome oxidases, and reductases. Substrates for all of these enzymes are known to those of skill in the art.

Example 1

Strips of Whatman Chromatography Paper No. 1 (GE Healthcare, Piscataway, N.J., USA), 0.18 mm in thickness, were marked with a black crayon to outline a rectangular channel 3-4 mm in width and 50 mm in length. The strips were placed on a hot plate for 20-30 seconds to melt the crayon wax and to allow it to penetrate the paper. The paper was then cooled, allowing the wax to harden into barriers extending the thickness of the paper and defining the outlines of the channels. Channels on four of the strips were then loaded with anti-β-galactosidase rabbit IgG (Life Technologies Corporation, Carlsbad, Calif., USA), using dilutions of 1:200, 1:800, 1:3200, and 1:12,800, respectively, in the strips, with 50 μL in each channel.

Separately, a polyacrylamide slab gel measuring 8.6 cm×6.7 cm×0.1 cm was loaded with β-galactosidase in each of four lanes at 0.1 μg per lane. Electrophoresis was performed in the gel at 300V for 25 minutes. The resulting β-galactosidase bands were then transferred from the gel to a PVDF membrane by Western blotting using a TRANS-BLOT® TURBO™ Transfer System (Bio-Rad Laboratories, Inc.) at 25V for three minutes, and the membrane was then blocked by treatment with Rockland blocking buffer (Rockland Immunochemicals Inc., Gilbertsville, Pa., USA) for one hour.

The impregnated strips containing the anti-β-galactosidase rabbit IgG were then placed over the membrane with one strip over each lane and therefore at a different dilution for each lane, the anti-β-galactosidase rabbit IgG thus serving as the primary antibody. The combined strips and membrane were then placed between pads soaked with Tris-Glycine and returned to the TRANS-BLOT® TURBO™ Transfer System where they were exposed to a current of 0.3 amperes for three minutes. The strips and membrane were then removed from the transfer system, the strips were removed from the membrane, and the entire membrane was washed with Tris-buffered saline with Tween 20 (TTBS) and then treated with 10 mL of ALEXA FLUOR® 488 goat anti-rabbit IgG (Life Technologies Corporation) as a secondary antibody at a dilution of 1:200.

Upon observation, detectable images of the β-galactosidase bands were obtained in all four lanes.

Example 2

Wax bordered channels were formed in strips of Whatman Chromatography Paper No. 1 as in Example 1, and the channels were impregnated with the secondary antibody of Example 1 at dilutions of 1:20 and 1:40, with 50 μL per channel, rather than the primary antibody. An additional strip was impregnated with goat anti-rabbit antibody labeled with horseradish peroxidase at a 1:40 dilution. A polyacrylamide slab gel of the same dimensions as that of Example 1 was loaded with β-galactosidase in each of three lanes at 0.1 μg per lane, electrophoresis was performed, and the resulting β-galactosidase bands were transferred to a PVDF membrane, as in Example 1.

The entire membrane was then treated with anti-β-galactosidase rabbit IgG as the primary antibody at a dilution of 1:5000 for one hour, then rinsed, after which the strips of secondary antibody were placed over individual lanes. The membrane with overlying strips were then returned to the TRANS-BLOT® TURBO™ Transfer System where they were run at 0.3 amperes for three minutes. The membrane and strips were then removed from the transfer system, the strips removed from the membrane, and the region with HRP-labeled antibody was treated with IMMUN-STAR™ Chemiluminescent Kit of Bio-Rad Laboratories, Inc. Upon observation, detectable images of the β-galactosidase bands were obtained in all lanes.

Example 3

Wax bordered channels were formed in strips of Whatman Chromatography Paper No. 1 as in Examples 1 and 2, and the channels were impregnated with mixtures containing both primary and secondary antibody. The primary antibody in all mixtures was 1:400 anti-β-galactosidase, and three different secondary antibodies were used, one in each mixture, as follows: ALEXA FLUOR® 488 goat anti-rabbit IgG, ALEXA FLUOR® 546 goat anti-rabbit IgG, and ALEXA FLUOR® 647 goat anti-rabbit IgG, all at 1:200 dilution. The volume of each mixture applied to its respective channel was 20 microliters. The strips were placed over individual lanes of a PVDF blotting membrane on which β-galactosidase bands had been blotted from an electrophoresis gel, and placed in the TRANS-BLOT® TURBO™ Transfer System where they were run at 0.1 amperes for five minutes. When the membrane and bands were removed from the Transfer System and the strips removed from the membrane, the three different colors of the labels on the secondary antibodies were each visible on the membrane as distinct bands.

In the claims appended hereto, the term "a" or "an" is intended to mean "one or more." The term "comprise" and variations thereof such as "comprises" and "comprising," when preceding the recitation of a step or an element, are intended to mean that the addition of further steps or elements is optional and not excluded. All patents, patent applications, and other published reference materials cited in this specification are hereby incorporated herein by reference in their entirety. Any discrepancy between any reference material cited herein or any prior art in general and an explicit teaching of this specification is intended to be resolved in favor of the teaching in this specification. This includes any discrepancy between an art-understood definition of a word or phrase and a definition explicitly provided in this specification of the same word or phrase.

What is claimed is:

1. A method for determining whether an antigen is immobilized on a blotting membrane by contacting an antibody with said antigen, said method comprising:
   (a) placing said blotting membrane in contact with a porous hydrophilic sheet having a laterally delimited region therein that is bordered by a hydrophobic or impermeable barrier and in which said antibody is retained, while aligning said laterally delimited region with a spot on said blotting membrane where said antigen resides if so immobilized on said blotting membrane;

(b) causing transfer of said antibody from said laterally delimited region of said porous hydrophilic sheet to said spot, wherein the causing transfer comprises placing a first buffer solution-wetted sheet of absorbent material on a side of said blotting membrane opposite the side in contact with said porous hydrophilic sheet, and a second buffer solution-wetted sheet of absorbent material on a side of said porous hydrophilic sheet opposite the side in contact with said blotting membrane, to form a transfer stack, and passing an electrical current across said transfer stack in a direction causing said transfer; and (c) detecting any occurrence of a binding reaction between said antibody and said antigen as an indication of the presence of said antigen in said spot.

2. The method of claim 1 wherein the barrier is hydrophobic.

3. The method of claim 2 wherein the hydrophobic barrier is wax or silanized transfer sheet.

4. The method of claim 3 wherein the silanized transfer sheet comprises silanized cellulose.

5. The method of claim 1 wherein said antibody comprises a member selected from the group consisting of a colorimetic label, a fluorogenic label, a chemiluminescent label, and a radiologic label.

* * * * *